(12) United States Patent
Baghel et al.

(10) Patent No.: US 6,272,938 B1
(45) Date of Patent: Aug. 14, 2001

(54) MONITORING OF VOLATILE ORGANIC COMPOUNDS IN GROUNDWATER WITH AN IN-SITU SAMPLING DEVICE

(75) Inventors: Sunita Singh Baghel, Rensselaer; Patricia Denise Mackenzie; Timothy Mark Sivavec, both of Clifton Park; Angelo Anthony Bracco, Albany; Joseph James Salvo, Schenectady, all of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/543,963

(22) Filed: Apr. 7, 2000

(51) Int. Cl.$^7$ ................................. G01N 1/00; G01N 1/12
(52) U.S. Cl. ................................. 73/863.23; 73/863.21; 73/863.56; 73/864.51
(58) Field of Search ................... 73/863.21, 863.23, 73/863.56, 863.71, 864.51, 863, 864

(56) References Cited

U.S. PATENT DOCUMENTS

| | | | |
|---|---|---|---|
| 5,010,776 | * 4/1991 | Lucero et al. | 73/863.23 |
| 5,059,790 | * 10/1991 | Klainer et al. | 250/227.21 |
| 5,481,927 | 1/1996 | Hubbell et al. | 73/863.71 |
| 5,804,743 | 9/1998 | Vroblesky et al. | 73/863.23 |
| 5,996,423 | * 12/1999 | Baghel et al. | 73/863.23 |

* cited by examiner

*Primary Examiner*—Hezron Williams
*Assistant Examiner*—Dennis Loo
(74) *Attorney, Agent, or Firm*—Bernadette M. Bennett; Noreen C. Johnson

(57) ABSTRACT

A sampling device can monitor contaminants in groundwater. The sampling device comprises a semi-permeable membrane for contact with groundwater, in which the semi-permeable membrane is permeable to contaminants and impermeable to groundwater; an inner chamber formed by the semi-permeable membrane for containing the contaminants from the groundwater that diffuse through the semi-permeable membrane; and a sensor device communicating with the inner chamber. The sensor device is in contact with the contaminants contained within the inner chamber for monitoring the contaminants.

18 Claims, 3 Drawing Sheets

MONITORING OF VOLATILE ORGANIC COMPOUNDS IN GROUNDWATER WITH AN IN-SITU SAMPLING DEVICE

BACKGROUND OF THE INVENTION

The invention relates to an in-situ sampling device for monitoring compounds. In particular, the invention relates to a method and device for monitoring of volatile organic compounds in groundwater wells.

Presently, large amounts of time, energy, and money are spent monitoring groundwater, for example monitoring groundwater at remediation sites. In recent years, attempts have been made to develop in-situ samplers that can passively sample volatile organic compounds (VOCs) in groundwater wells. Diffusive vapor samplers with sorbent tube and water samplers, as disclosed in U.S. Pat. Nos. 5,481,927 and 5,804,743, provide passive in-situ methods for monitoring VOCs in groundwater and unsaturated soils (vadose) zones.

The diffusive vapor sampler of U.S. Pat. No. 5,804,743, assigned to the assignee of this invention, comprises a diffusion membrane that has a high permeability rate for organic vapors and is impermeable to water. Upon retrieval from the well, the samples are sent to a laboratory for analysis or analyzed by gas chromatography on site.

Diffusive vapor samplers provide advantages over traditional groundwater sampling methods because these samplers do not need purging of groundwater wells in order to collect representative water samples. Purging can increase project costs because removal of water from each well results in large amounts of contaminated purge water that must be disposed. Moreover, purging potentially confounds analytical results by creating sediments, particulates, and erroneous concentration readings. Although in-situ diffusive vapor samplers promote minimization of wastes, they may not provide yield real-time monitoring of groundwater wells.

Therefore, a need exists for methods to monitor groundwater and remediation processes. Further, a need exists for an in-situ device that can be used to monitor volatile organic compounds (VOCs) continuously in groundwater.

SUMMARY OF THE INVENTION

An aspect of the invention provides a sampling device that can monitor contaminants in groundwater. The sampling device comprises a semi-permeable membrane for contact with groundwater, in which the semi-permeable membrane is permeable to contaminants and impermeable to groundwater; an inner chamber formed by the semi-permeable membrane for containing the contaminants from the groundwater that diffuse through the semi-permeable membrane; and a sensor device communicating with the inner chamber. The sensor device is in contact with the contaminants contained within the inner chamber for monitoring the contaminants.

Further, the invention provides a method for the monitoring of contaminants in ground water. The method comprises steps of: providing a semi-permeable membrane, the membrane being permeable only to the contaminants in groundwater; forming an inner chamber with the semi-permeable membrane for containing the contaminants that diffuse into the chamber; disposing the semi-permeable membrane within the groundwater; and detecting the contaminants with a sensor device. The sensor device is in communication with the inner chamber of the semi-permeable membrane for the monitoring of contaminants in groundwater.

Yet another aspect of the invention sets forth a sampling system for the monitoring of contaminants in groundwater and transmission of information from the monitoring. The sampling system comprises a sampling device and a data receiving and transmission system. The sampling device comprises a semi-permeable membrane for contact with groundwater, the semi-permeable membrane being permeable to contaminants and impermeable to groundwater; an inner chamber formed by the semi-permeable membrane for containing the contaminants from the groundwater that diffuse through the semi-permeable membrane; and a sensor device communicating with the inner chamber, the sensor device being in contact with the contaminants contained within the inner chamber. The data receiving and transmission system communicates monitored information from the sampling system.

BRIEF DESCRIPTION OF THE DRAWINGS

Other features and advantages of the present invention will become apparent from the following description of embodiments of the invention, which refers to the accompanying drawings, wherein.

DETAILED DESCRIPTION OF THE INVENTION

An in-situ sampling device, as embodied by the invention, can provide monitoring of contaminants, such as, but not limited to, solvents in groundwater, in which the monitoring can be at least one of continuous and non-continuous monitoring. The in-situ sampling device includes a sampling chamber that encloses a sensor device, for example at least one of a gas sensor and a gas chromatograph (gc). Alternatively, the in-situ sampling device comprises a chamber that is connected to a sensor device, such as, but not limited to, at least one of a gas sensor and gas chromatograph (gc) through tubing. The sensor device will be discussed hereinafter as one or both of gas chromatograph and a gas sensor, however, this description is merely exemplary, and is not intended to limit the invention in any manner.

Figure 1:
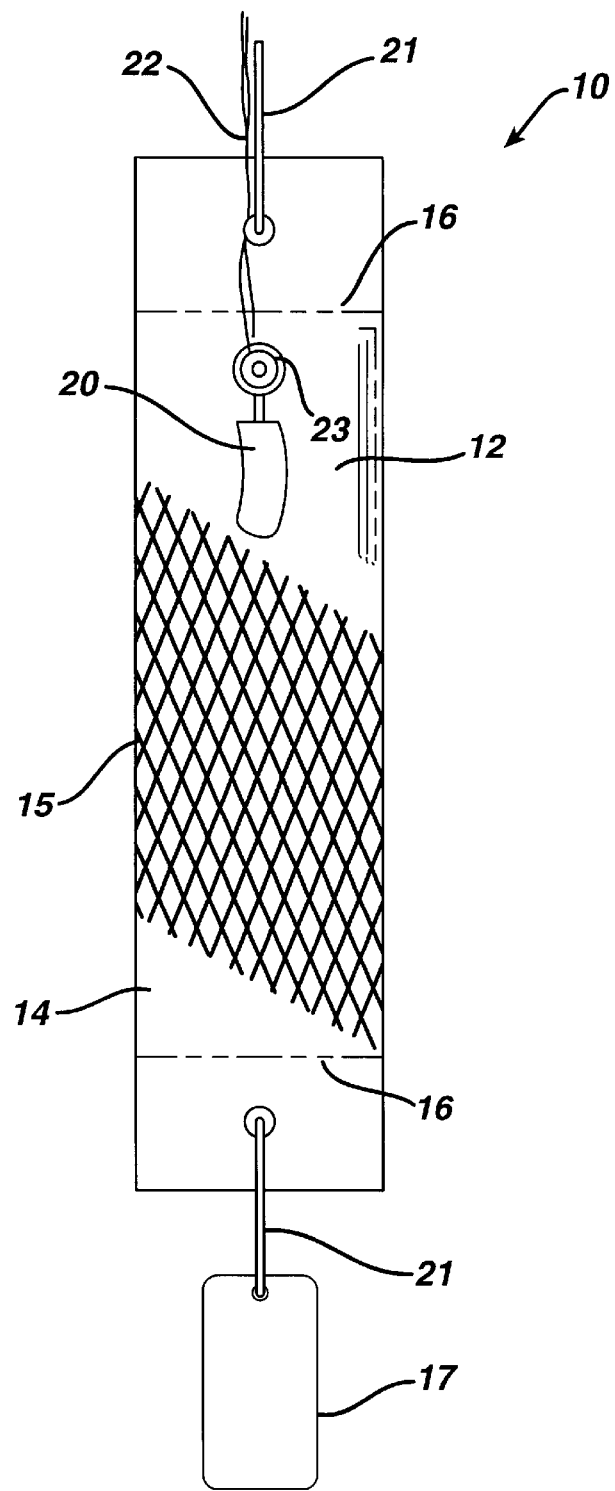
FIG. 1 is a cross-sectional view of an embodiment of a sampling device, as embodied by the invention.

As illustrated in FIG. 1, the in-situ sampling device 10 comprises a gas sensor 20 disposed within the sampling chamber 12 of a semi-permeable membrane 14. The sensor 20 detects contaminants in the groundwater, such as, but not limited to, chlorinated solvents, hydrocarbons, VOCs, light non-aqueous phase liquid (LNAPL), and dense non-aqueous phase liquid (DNAPL). The contaminant is referred to hereinafter as a VOC, however, this description is merely exemplary, and is not intended to limit the invention in any manner. Further, although only one sensor is illustrated, the scope of the invention comprises an in-situ sampling device comprising a plurality of sensors.

The in-situ sampling device 10 comprises a semi-permeable, hydrophobic membrane 14 (hereinafter "semi-permeable membrane"), which can comprise low-density polyethylene. Alternatively, the semi-permeable membrane 14 can comprise any appropriate material, such as, but not limited to, silicone, polyethylene, and Mylar®. The semi-permeable membrane material is selected so VOCs can diffuse therethrough, with the semi-permeable membrane material being generally impermeable to water. This semi-permeable membrane feature makes the membrane effective in protecting an in-situ sampling device if exposed to at least one of groundwater and heavy particulate. The impermeable feature also expands utility of the in-situ sampling device into areas and applications where environmental considerations previously limited use.

The gas sensor 20 can comprise a metal oxide semiconductor (MOS) hydrocarbon sensor. The gas sensor 20 can be located within the sampling chamber 12 that is formed by membrane 14. The gas sensor 20 can be located in a approximate middle portion of the sampling chamber 12 formed by the semi-permeable membrane 14. As illustrated in FIG. 1, the membrane 14 can be covered with a mesh protective sleeve or cover 15 (hereinafter "mesh cover"). The mesh cover 15 can prevent abrasion or puncturing of the semi-permeable membrane 14 and the chamber formed thereby. Although not illustrated, the in-situ sampling chamber 12 can enclose a gas that is disposed over an open end of the gas sensor 20.

To use the in-situ sampling device 10 in a well, a support line 21 is attached to the in-situ sampling device 10. The support line 21 comprises a suitable length of line 21 to support the in-situ sampling device 10. The support line 21 can be formed of any appropriate material, for example, but not limited to, nylon and other inert materials. The support line 21 can support the mesh cover 15, for example by an appropriate fastening structure. The support line 21 can be used to raise the in-situ sampling device 10 out of a well after a sampling operation. Further, a weight 17 can be hung from a lower portion of the mesh cover 15 and in-situ sampling device 10 to assist in submerging the in-situ sampling device 10 in the well.

The chamber of semi-permeable membrane 14 is filled, for example partially or completely, prior to placement of the in-situ sampling device 10 within a well. The chamber 12 can be filled with a reference fluid, for example, but not limited to, air. The semi-permeable membrane 14 can be permeable to the reference fluid, and can be impermeable to groundwater. Thus, only contaminants can flow therethrough.

Once the in-situ sampling device 10 is in contact with contaminated groundwater, contaminants can begin to diffuse through the semi-permeable membrane 14 into chamber 12. Air that is displaced from the in-situ sampling device 10 diffuses into the groundwater, as contaminants from the groundwater diffuse into the chamber 12 of the in-situ sampling device 10. The contaminants continue to diffuse into the chamber 12 until a concentration of contaminants in the chamber 12 and concentration of contaminants in the groundwater reach a state of equilibrium at which time the diffusion halts.

The semi-permeable membrane 14 comprises a seal 16 disposed on both ends. The seal 16 may be formed by any appropriate sealing function, such as but not limited to, by an impulse heat sealer to form the chamber 12. An adhesive seal 16 (not illustrated) can also seal the semi-permeable membrane 14.

Figure 2:
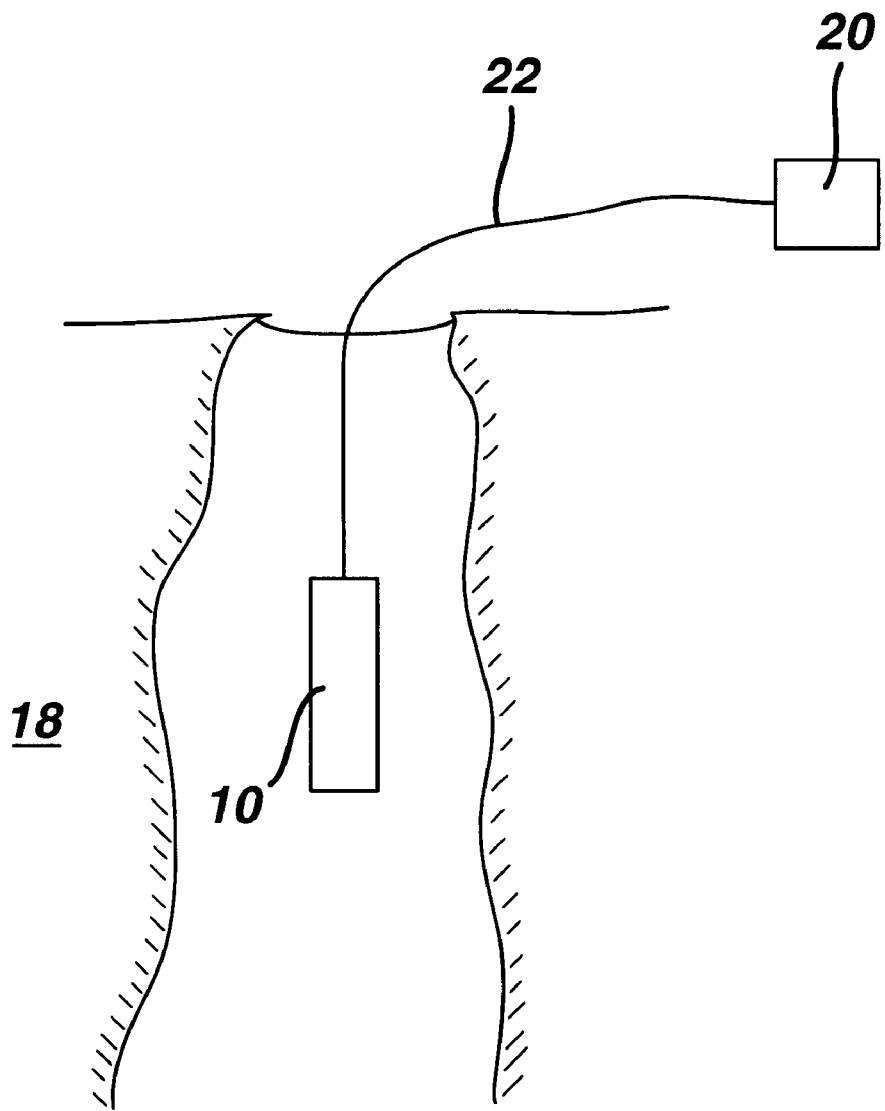
FIG. 2 is a cross-sectional view of another embodiment of a sampling device, as embodied by the invention.

FIG. 2 illustrates a further in-situ sampling device 10, as embodied by the invention. Like elements will be provided with like reference characters. In FIG. 2, the sampling device 10 is placed into a well 18 and connected to a gas sensor or gas chromatograph for monitoring groundwater contamination. The in-situ sampling device 10 of FIG. 2 comprises a length of tubing 22 that is connected to sampling chamber 12. The length of tubing 22 is connected to the sampling chamber 12 through a compressor fitting 23. The in-situ sampler 10 can then be connected to a gas chromatograph through the length of tubing 22. A sensing device, including at least one of a gas chromatograph, a micro-gas chromatograph, and a gas sensor, can take a sample via an automated pump (not illustrated) that can be installed therewith. The above description of the gas chromatograph is merely illustrative, and is not intended to limit the invention. The scope of the invention comprises any kind of sensing device that can detect hydrocarbon, as embodied by the invention.

Figure 3:
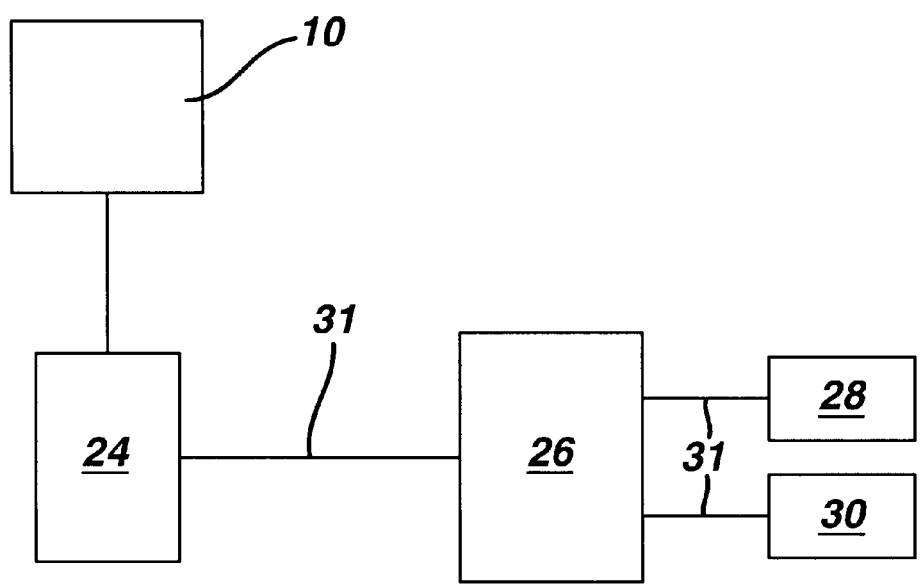
FIG. 3 is a perspective view of a sampling system, as embodied by the invention.

FIG. 3 illustrates a transceiver 24, which sends data signal(s) from the gas sensor 20 to a data collection station 26, for use with the in-situ sampling device 10, as embodied by the invention. The transceiver 24 can send these signals by any appropriate communications link 31. The communications link 31, and other communications links described herein, comprise, but are not limited to, at least one of a phone modem, wired networks, modem, radio, network connection, communication, radio communication and other wireless communication systems, cellular communication, satellite communication, web access communication, and Internet access communication, and combinations thereof.

The gas sensor 20 can be connected to an explosion-proof transmitter via sensor wires on a well head. The sensor transmitters can be mounted at any suitable distance from the collection system. The sensor transmitters provide linear output signals over a range of gas concentrations, regardless of a sensor type. The sensor transmitters can be connected to a data logger, such as, but not limited to, a database, Web page, or other storage device, for recording of the information. Further, any party so authorized by the in-situ sampling device 10 owner or operator can access the data logger to review the information. For example, regulatory agencies can access the data logger.

A data receiving and transmission system can comprise a data transmission system 28 and a data processing and reporting system 30 that are also provided in the in-situ sampling device 10 for communicate of data and information. Any suitable data transmission system 28 and a data processing and reporting system 30 for data transmission and retrieval can be used with the in-situ sampling device 10. For example, a data transmission system 28 and a data processing and reporting system 30 as set forth in U.S. Ser. No. 09/201,385, entitled "Monitoring, Diagnostic, and Reporting System and Process" and U.S. Pat. No. 5,999,643, entitled Passive Water Sampler and method of Sampling (both of which are assigned to the assignee of the present invention) can be used with the in-situ sampling device 10, as embodied by the invention. The teachings of both U.S. Ser. No. 09/201,385 and U.S. Pat. No. 5,999,643 are fully incorporated by reference herein.

The method of sampling groundwater contaminants, as embodied by the invention, comprises positioning an in-situ sampling device 10 in a well 18. The in-situ sampling device 10 is positioned in the well 18 so the semi-permeable membrane 14 contacts contaminated groundwater. The semi-permeable membrane 14 has been configured to form an inner chamber 12 prior to insertion of the in-situ sampling device 10 in the groundwater. The inner chamber 12 contains the contaminants that diffuse through semi-permeable membrane 14 during use of the insitu sampling device 10. The in-situ sampling device 10 remains in the well for a time that is sufficient to allow contaminants in the groundwater to diffuse through the semi-permeable membrane 14 and reach an equilibrium state.

The gas sensor 20, which can be disposed within chamber 12 and alternatively disposed outside of the well 18. The gas sensor 20 can provide total hydrocarbons in the groundwater. Alternatively, the gas sensor 20 can quantitatively identify individual contaminant species in the groundwater in a relatively continuous manner. The in-situ sampling device 10 provides information about contaminants in the groundwater in a relatively fast manner, such as but not limited to real-time and near real-time. The term "real-time" means that any delays from the time the information is attained, and then made available is minimal, for example on the order of minutes, and possibly a few seconds, or even longer, if the need for the information is defined as such and the data may still be relevant and of value to the interested party, if any delay is present. Also, the term real time can mean a time required by a user to obtain data.

The in-situ sampling device 10, as embodied by the invention, has been described with respect to monitoring groundwater wells. The scope of the invention comprises use of the in-situ sampling device 10 in other such applications. For example, and in no way limiting of the invention, the in-situ sampling device 10 can be used chemical process applications to determine contaminants.

While various embodiments are described herein, it will be appreciated from the specification that various combinations of elements, variations or improvements therein may be made by those skilled in the art, and are within the scope of the invention.

What is claimed is:

1. A sampling device for the monitoring of contaminants in groundwater, the sampling device comprising:
   a semi-permeable membrane for contact with groundwater, the semi-permeable membrane being permeable to contaminants and impermeable to groundwater;
   an inner chamber formed by the semi-permeable membrane for containing the contaminants from the groundwater that diffuse through the semi-permeable membrane; and
   a sensor device communicating with the inner chamber, the sensor device being in contact with the contaminants contained within the inner chamber for monitoring the contaminants.

2. The sampling device according to claim 1, wherein the semi-permeable membrane comprises polyethylene.

3. The sampling device according to claim 1, wherein the sensor device is disposed in the inner chamber.

4. The sampling device according to claim 1, the sampling device further comprising tubing, wherein the sensor device is connected to the inner chamber via the tubing.

5. A sampling device for the monitoring of contaminants in groundwater, the sampling device comprising:
   a semi-permeable membrane for contact with groundwater, the semi-permeable membrane being permeable to contaminants and impermeable to groundwater;
   an inner chamber formed by in semi-permeable membrane for containing the contaminants from the groundwater that diffuse through the semi-permeable membrane; and
   a sensor device comprising a metal oxide semiconductor sensor wherein the sensor device communicates with the inner chamber, the sensor device being in contact with the contaminants contained within the inner chamber for monitoring the contaminants.

6. The sampling device according to claim 1, the sampling device further comprising a protective covering disposed on the semi-permeable membrane.

7. The sampling device according to claim 1, wherein the sampling device continuously monitors the groundwater.

8. A method for the monitoring of contaminants in ground water, the method comprising the steps of:
   providing a semi-permeable membrane, the membrane being permeable only to the contaminants in groundwater;
   forming an inner chamber with the semi-permeable membrane for containing the contaminants that diffuse into the chamber;
   disposing the semi-permeable membrane within the groundwater; and
   detecting the contaminants with a sensor device, the sensor device being in communication with the inner chamber of the semi-permeable membrane for the monitoring of contaminants in groundwater.

9. The method according to claim 8, wherein the step of detecting the contaminants comprises positioning the sensor device within the inner chamber in contact with the contaminants.

10. The method according to claim 8, wherein the step of detecting the contaminants comprises connecting the sensor device with the inner chamber of the membrane.

11. The method according to claim 8, further comprising a step of receiving data from the sensor device and transmitting the data to a remote location.

12. The method according to claim 8, wherein the step of detecting the contaminants comprises determining a total amount of hydrocarbons present within the groundwater.

13. The method according to claim 8, wherein the step of detecting the contaminants comprises identifying individual species quantitatively in the groundwater in a manner.

14. The method according to claim 8, wherein the monitoring comprises continuous monitoring.

15. A sampling system for the monitoring of contaminants in groundwater and transmission of information from the monitoring, the sampling system comprising:
   a sampling device comprising:
      semi-permeable membrane for contact with groundwater, the semi-permeable membrane being permeable to contaminants and impermeable to groundwater;
      an inner chamber formed by the semi-permeable membrane for containing the contaminants from the groundwater that diffuse through the semi-permeable membrane; and
      a sensor device communicating with the inner chamber, the sensor device being in contact with the contaminants contained within the inner chamber; and
   a data receiving and transmission system that communicates monitored data from the sampling device.

16. A sampling system according to claim 15, wherein the data receiving and transmission system provides the data via communications link in at least one of near real-time and real time.

17. A sampling system according to claim 15, wherein the communications link comprises at least one of phone modem, wired networks, modem, radio, network connection, communication, radio communication and other wireless communication systems, cellular communication, satellite communication, web access communication, and Internet access communication, and combinations thereof.

18. A sampling system according to claim 15, wherein the data receiving and transmission system can transmit the data to a remote location from the sensor device.

* * * * *